United States Patent [19]

Kleiner et al.

[11] Patent Number: 4,548,762

[45] Date of Patent: Oct. 22, 1985

[54] PROCESS FOR THE PREPARATION OF VINYLPHOSPHONIC ACID DICHLORIDE AND 2-CHLOROETHANEPHOSPHONIC ACID DICHLORIDE

[75] Inventors: Hans-Jerg Kleiner, Kronberg; Walter Dürsch, Königstein, both of Fed. Rep. of Germany

[73] Assignee: Hoechst Aktiengesellschaft, Fed. Rep. of Germany

[21] Appl. No.: 463,993

[22] Filed: Feb. 4, 1983

Related U.S. Application Data

[63] Continuation of Ser. No. 297,734, Aug. 31, 1981, abandoned.

[30] Foreign Application Priority Data

Sep. 6, 1980 [DE] Fed. Rep. of Germany ....... 3033614

[51] Int. Cl.$^4$ ................................................ C07R 9/42
[52] U.S. Cl. .......................... 260/543 P; 260/502.4 R
[58] Field of Search ............. 260/543 P; 260/502.4 R

[56] References Cited

U.S. PATENT DOCUMENTS

| | | | |
|---|---|---|---|
| 3,950,413 | 4/1976 | Finke et al. | 260/543 P |
| 4,013,715 | 3/1977 | Finke et al. | 260/543 P |
| 4,069,247 | 1/1978 | Kleiner | 260/502.4 R |

*Primary Examiner*—Donald B. Moyer
*Assistant Examiner*—C. Joseph Faraci
*Attorney, Agent, or Firm*—Connolly and Hutz

[57] ABSTRACT

A process for the preparation of vinylphosphonic acid dichloride and 2-chloroethanephosphonic acid dichloride, wherein 2-chloroethanephosphonic acid derivatives containing 2-chloroethyl ester groups, as produced in the Arbusow rearrangement of tris-chloroethyl phosphite, are heated to 150° to 230° C. in a first stage, and, in a second stage, the residual reaction mixture is reacted with phosgene at 90°–200° C., in the presence of basic catalysts or of alkali metal salts as catalysts, and in the presence of phosphonic acid dichlorides.

5 Claims, No Drawings

PROCESS FOR THE PREPARATION OF VINYLPHOSPHONIC ACID DICHLORIDE AND 2-CHLOROETHANEPHOSPHONIC ACID DICHLORIDE

This application is a continuation of application Ser. No. 297,734 filed Aug. 31, 1981, now abandoned.

2-Chloroethanephosphonic acid derivatives containing 2-chloroethyl ester groups are valuable starting materials for the preparation of 2-chloroethanephosphonic acid dichloride, from which vinylphosphonic acid dichloride can be prepared by cleavage of hydrogen chloride (DE-BP No. 2,132,962; DE-BP No. 2,357,678). In this process, considerable quantities of 1,2-dichloroethane are produced during the preparation of the 2-chloroethanephosphonic acid dichloride, the former compound affecting the space/time yield of the process unfavorably. In addition, a further step-that of hydrogen chloride cleavage at high temperatures-is necessary to obtain the desired end product, namely the vinylphosphonic acid dichloride. Processes are therefore sought which, although using as starting materials 2-chloroethanephosphonic acid derivatives which contain 2-chloroethyl ester groups, lead, in a simple manner, directly to vinylphosphonic acid dichloride.

It has now been found that vinylphosphonic acid dichloride and 2-chloroethanephosphonic acid dichloride can be prepared in a simple and economical manner by heating 2-chloroethanephosphonic acid derivatives containing 2-chloroethyl ester groups to 150° to 230° C., preferably 170° to 215° C., if appropriate in the presence of catalysts, and reacting the residual reaction mixture with phosgene at 90°–100° C., preferably 120°–170° C., in the presence of basic catalysts or alkali metal salts and in the presence of phosphonic acid dichlorides.

The 2-chloroethanephosphonic acid derivatives which serve as starting material and which contain 2-chloroethyl ester groups, are prepared by the known Arbusow rearrangement of tris-chloroethyl phosphite. Bis-2-chloroethyl 2-chloroethanephosphonate is obtained as the most important compound in this rearrangement. Furthermore, non-distillable so-called polycondensates of essentially unknown structures, among these also the compound of the formula

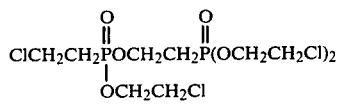

are also frequently obtained in the Arbusow rearrangement of tris-chloroethyl phosphite. All these products, alone or mixed with one another, can serve as the starting material for the preparation of the vinylphosphonic acid derivatives. Mono-2-chloroethyl 2-chloroethanephosphonate can also be used.

However, the total reaction mixture of the Arbusow rearrangement, as produced in the rearrangement, that is to say, as a rule, the bis-2-chloroethyl 2-chloroethanephosphonate mixed with the non-distillable so-called polycondensates, is preferred as the starting material.

Numerous compounds are suitable as acid or basic catalysts for this stage. The following are examples of compounds which can be used as acid catalysts:

(A) Sulfuric acid, phosphoric acid, hydrochloric acid and hydrobromic acid;

(B) halogen-containing carboxylic acids with a $P_{Ka}$ value <2.5, such as dichloroacetic acid, trichloroacetic acid and trifluoroacetic acid;

(C) aromatic sulfonic acids with a $P_{Ka}$ value <2.5, such as benzenesulfonic acid and p-toluenesulfonic acid;

(D) preferably phosphinic acids having 2 to 18 carbon atoms, such as dimethylphosphinic acid, methylethylphosphinic acid, dioctylphosphinic acid, methylphenylphosphinic acid and diphenylphosphinic acid;

(E) particularly preferably phosphonic acids having 1 to 18 carbon atoms and half-esters thereof having 1 to 4 carbon atoms in the alcohol radical, such as methanephosphonic acid, propanephosphonic acid, monomethyl propanephosphonate, octadecanephosphonic acid, 2-chloroethanephosphonic acid, mono-2-chloroethyl 2-chloroethanephosphonate, vinylphosphonic acid, mono-2-chloroethyl vinylphosphonate, monoethyl vinylphosphonate and benzenephosphonic acid.

(F) Pyrophosphonic acids or half-esters thereof, such as 2-chloroethanepyrophosphonic acid, benzenepyrophosphonic acid, vinylpyrophosphonic acid and mono-2-chloroethyl vinylpyrophosphonate, are also particularly preferred.

(G) The alkali metal salts, preferably sodium or potassium salts, of the acids mentioned under A to F are also suitable.

(H) The acid reaction mixtures which are formed in the process according to the invention are also very suitable.

The following can be used as basic catalyts:

(A) tertiary aliphatic and aromatic amines and phosphines having 3 to 18 carbon atoms, such as trimethylamine, tripropylamine, tributylamine, triphenylamine, trimethylphosphine, triethylphosphine, tripropylphosphine, tributylphosphine, triphenylphosphine and tris-(p-dimethylaminophenyl)-phosphine, and the corresponding mixed amines, phosphines, phospholanes and phospholenes, such as dimethylethylamine, diethylbutylamine, N-dimethylaniline, 4-methyl-N-dimethylaniline, N-diethylaniline, N,N-tetramethylphenyldiamine or N-methylpyrrolidine; methyldiethylphosphine, dimethylpropylphosphine, diethylbenzylphosphine, 1-methyl-phosphol-3-ene and 2-ethyl-3-methylphosphol-3-ene.

(B) Quaternary ammonium salts or phosphonium salts having 3 to 18 carbon atoms, such as tetramethylammonium chloride or bromide, tetraethylphosphonium chloride, trimethylbenzylammonium chloride, triethylbenzylammonium chloride, triethylbenzylammonium bromide, trimethylbenzylphosphonium chloride and triphenylethylphosphonium 2,4-diaminobenzenesulfonate;

(C) heterocyclic compounds with an aromatic character, such as pyridine, 4-(dimethylamino)-pyridine and quinoline, and their various alkyl and dialkyl derivatives, preferably methyl or dimethyl derivatives, and imidazole, N-vinylimidazole, benzthiazole, 2-amino-6-ethoxybenzthiazole, and also phosphabenzoles;

(D) acid amides, such as dimethylformamide, diethylformamide, N-dimethylacetamide, N-diethylpropionamide, N-methylbenzamide, N-methylpyrrolidone and N,N'-tetramethylterephthalic acid diamide, or ureas, such as tetramethylurea and trimethylphenylurea;

(E) other nitrogen compounds or phosphorus compounds with an N atom or P atom with a valency higher than 3, such as pyridine-N-oxide, trimethylphosphine oxide, tributylphosphine oxide, trihexylphosphine oxide, triphenylphosphine oxide, trihexylphosphine oxide, trimethylphosphine oxide, dimethylphenylphosphine oxide, dimethylphenylphosphine sulfide, dimethylchloromethylphosphine oxide, dimethyleicosylphosphine oxide, dimethyldodecylphosphine oxide, dimethylphosphine oxide, dimethylpyrrolidinyl-1-methylphosphine oxide, triphenylphosphine dichloride, dimethyldodecylphosphine sulfide, triphenylphosphinimine, dimethylchloromethylphosphine dichloride, N-2-dimethylphosphinylethyl-methyl-acetamide and N-2-dimethylphosphinyl-ethylmethyl-amine, and phospholene oxides, such as 1-methylphosphol-1-ene oxide and 1-ethyl-3-methyl-phosphol-1-ene oxide;

(F) amides of phosphinous and phosphonous acid and phosphinic acids and phosphonic acids and their thio analogues, such as ethanephosphonic acid bis-diethylamide, methanebutane-phosphinous acid dimethylamide and diethylphosphinous acid isobutylamide, and also triamides of phosphoric acid and thiophosphoric acid, such as hexamethylphosphoric acid triamide.

(G) Alkali metal carbonates, preferably sodium carbonate and potassium carbonate, alkali metal hydroxides, preferably sodium hydroxide and potassium hydroxide, and alkali metal alcoholates, preferably sodium methylate.

The salts of hypophosphorus acid, for example sodium hypophosphite and potassium hypophosphite, are also suitable as catalysts. These catalysts are also particularly preferred as additives which largely prevent a dark discoloration of the reaction materials.

The catalysts are employed in quantities of from 0.01 to 10, preferably 0.1 to 5, % by weight. When using the acid reaction mixtures which have already been obtained, relatively large quantities of from 10 to 50% by weight can also be employed.

The process is carried out, in general, by heating the starting materials to the reaction temperature. The cleavage of the 1,2-dichloroethane then begins, accompanied, as a rule, by the simultaneous cleavage of relatively small quantities of hydrogen chloride. The 1,2-dichloroethane which splits off distils off as a rule under normal pressure, if appropriate with the aid of an inert gas stream. Nitrogen is particularly suitable as the inert gas. In an individual case, it can be particularly advantageous, especially at the end of the reaction, to distil off the 1,2-dichloroethane in vacuo. The cleavage of the 1,2-dichloroethane has ended after about 5 to about 20 hours. In the case of complete cleavage of the 1,2-dichloroethane, the end product is then largely chlorine-free or poor in chlorine. However, it is not advantageous to carry out the cleavage of the 1,2-dichloroethane until the end product is completely free of chlorine, but only to a content of about 1 to about 10%, preferably 5 to 8%. This chlorine is present in the form of chloroethyl groups. End products which are largely free of chlorine are mostly less suitable for further processing, since they frequently have a dark discoloration and already tend to decompose at the high reaction temperatures.

The reaction temperatures are 150° to 230° C., preferably 170° to 215° C. Higher temperatures are possible, but are of no advantage. There is a danger of decomposition, and also of polymerization.

When using the catalysts previously mentioned, the reaction can be carried out at somewhat lower temperatures than is possible without catalysts. The catalysts frequently favorably affect the color of the end product. The process can be designed as a continuous process. The addition of polymerization inhibitors, such as, for example, hydroquinone, hydroquinone monomethyl ether or phenothiazine, can be advantageous.

The reaction products of this first stage or step consist of mixtures of vinylphosphonic acid derivatives, the type and the quantity of the individual constituent being unknown. In the ideal case, using bis-2-chloroethyl 2-chloroethanephosphonate as the starting material, a mixture of the compounds of the formulae

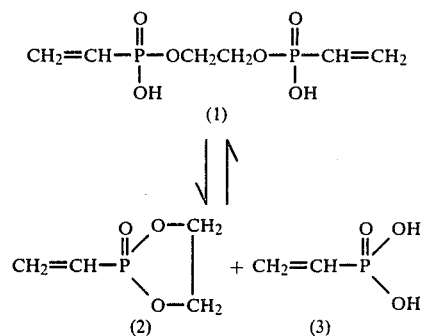

is obtained. The two compounds (2) and (3) exist in equilibrium with the compound (1). In addition, the reaction mixture also contains vinylpyrophosphonic acid or derivatives thereof. However, independently of the type of starting compounds used, all the individual compounds present in the reaction mixture contain vinylphosphonic acid groups and, depending on the chlorine content, a certain number of chloroethyl groups. The vinylphosphonic acid derivatives according to the invention are water-soluble, even with the chlorine content of 1 to 10% indicated.

The mixtures, thus obtained, of various vinylphosphonic acid derivatives are then directly phosgenated, without the isolation of individual compounds, in particular at temperatures of from 90° to 200° C., preferably 120° to 170° C., in the presence of basic catalysts or of alkali metal salts of the acids listed above under A to F or alkali metal salts of hypophosphorus acid as the catalyst, and in the presence of phosphonic acid dichlorides. If the first stage was already carried out in the presence of these catalysts, a further addition of catalysts in the second stage becomes superfluous.

Like the first reaction stage, the process can be designed as a continuous operation. The addition of the polymerization inhibitors already mentioned above can also be advantageous. The basic catalysts, as listed above for the first stage, and the alkali metal salts of the acids mentioned above under A to F are suitable as catalysts which must necessarily be present in this phosgenation. Furthermore, the alkali metal salts of hypophosphorus acid can also serve as the catalyst.

Basically, the phosgenation is carried out in such a manner that phosphonic acid dichlorides are added to the reaction mixture from the beginning. $C_1$-$C_{12}$-alkanephosphonic acid dichlorides, for example methanephosphonic acid dichloride, ethanephosphonic acid dichloride or propanephosphonic acid dichloride, preferably, however, vinylphosphonic acid dichloride, particularly preferably 2-chloroethanephosphonic acid dichloride, or mixtures of these acid chlorides are suitable for this purpose. The total quantity of these phosphonic acid dichlorides, relative to the vinylphosphonic acid derivatives (1st stage), is approximately 5 to 200, preferably 20 to 100, % by weight.

A mixture of vinylphosphonic acid dichloride and 2-chloroethanephosphonic acid dichloride is obtained in this phosgenation. Both compounds exist in equilibrium with one another in the reaction mixture. As a consequence of this equilibrium, the production of vinylphosphonic acid dichloride can be optimized by already adding a certain quantity of 2-chloroethanephosphonic acid dichloride at the beginning of the phosgenation. It has been found in practice that the best yield of vinylphosphonic acid dichloride is obtained if a mixture of vinylphosphonic acid dichloride and 2-chloroethanephosphonic acid dichloride is initially introduced. If desired, the quantity of phosphonic acid dichloride which must be present to achieve a maximum yield of vinylphosphonic acid dichloride and/or chloroethylphosphonic acid dichloride in the chlorination process can easily be determined by preliminary experiments. At the end of the phosgenation, the same quantity of chloroethanephosphonic acid dichloride is then obtained as was added at the beginning of the reaction, whilst in contrast significantly more vinylphosphonic acid dichloride is formed than was initially added. By initially introducing suitable quantities of vinylphosphonic acid dichloride, it is of course also possible to steer the reaction so that essentially or exclusively 2-chloroethanephosphonic acid dichloride is produced. The type and quantity of the phosphonic acid dichloride necessary for achieving a particular result depends in particular on the reaction conditions, such as time, temperature and type of catalyst. After the chlorination process has ended, a mixture of vinylphosphonic acid dichloride and chloroethylphosphonic acid dichloride is obtained, which mixture can easily be separated by distillation. Both compounds are important organophosphorus intermediates for the preparation of compounds for flameretarding finishing or for the preparation of chloroethanephosphonic acid, which is employed as a growth regulator in plant cultivation.

EXAMPLE 1

2.4 g of sodium hypophosphite monohydrate are added to 800 g of the mixture from the Arbusow rearrangement of tris-chloroethyl phosphite, which contains 50% of bis-2-chloroethyl 2-chloroethanephosphonate and 16% of 2-chloroethanephosphonic acid 2-chloroethyl ester 2-(bis-(2-chloroethoxy)-phosphono)-ethyl ester, and the mixture is heated to 160° C., whilst flushing with nitrogen and stirring. The cleavage of 1,2-dichloroethane begins. The temperature is now gradually increased to 180° C., and 1,100 g of the same Arbusow mixture, mixed with 3.3 g of sodium hypophosphite monohydrate, are uniformly added dropwise, whilst 1,2-dichloroethane distils off. The temperature is increased to 200° C. after 7.5 hours. After 12 hours, the mixture is cooled whilst being flushed with nitrogen. 821 g of dichloroethane with a content of 0.3% of hydrogen chloride is obtained in the receiving flask. A further 25 g of 1,2-dichloroethane are collected in a cold trap downstream from the receiving flask. 1,035 g of vinylphosphonic acid derivatives remain. 292 g of this reaction mixture are metered into a mixture of 250 g of 2-chloroethanephosphonic acid dichloride, 50 g of vinylphosphonic acid dichloride and 1 g of triphenylphosphine, during the course of 5 hours, the mixture being stirred at 140° C. whilst phosgene is simultaneously continuously introduced. Phosgene is then further introduced for 7 hours at this temperature. 1,2-Dichloroethane which is formed distils off during the phosgenation. After the phosgenation has ended, the excess phosgene is stripped off at room temperature in the vacuum from a water jet. The mixture is then distilled at 2 mm Hg with the aid of a column. 280 g of vinylphosphonic acid dichloride and 250 g of 2-chloroethanephosphonic acid dichloride are obtained. The distillation residue is 50 g. 230 g of vinylphosphonic acid dichloride were thus prepared from 292 g of vinylphosphonic acid derivatives. 50 g of vinylphosphonic acid dichloride and 250 g of 2-chloroethanephosphonic acid dichloride are again employed as the reaction medium in a second mixture.

EXAMPLE 2

297 g of the vinylphosphonic acid derivatives prepared in Example 1 are metered into a mixture of 250 g of 2-chloroethanephosphonic acid dichloride and 50 g of vinylphosphonic acid dichloride during the course of 3.5 hours, the mixture being stirred at 145° C. whilst phosgene is simultaneously continuously introduced. Phosgene is then further introduced for 12 hours at this temperature. 1,2-Dichloroethane which is formed distils off during the phosgenation. After the phosgenation has ended, the excess phosgene is stripped off at room temperature in the vacuum from a water jet. The mixture is then distilled at 2 mm Hg with the aid of a column. 307.5 g of vinylphosphonic acid dichloride and 250 g of 2-chloroethanephosphonic acid dichloride are obtained. The distillation residue is 62 g. 257.5 g of vinylphosphonic acid dichloride were thus prepared from 297 g of vinylphosphonic acid derivatives. 50 g of vinylphosphonic acid dichloride and 250 g of 2-chloroethanephosphonic acid dichloride are again employed as the reaction medium in a further mixture.

EXAMPLE 3

1,000 g of the mixture from the Arbusow rearrangement, as employed in Example 1, are heated to 214° C. under a nitrogen atmosphere and whilst stirring. 1,2-Dichloroethane begins to distil off. The temperature is lowered to 208° C. after 3 hours. A further 900 g of the mixture from the Arbusow rearrangement are then added dropwise at this temperature during the course of 2.5 hours, whilst 1,2-dichloroethane distils off. 830 g of 1,2-dichloroethane have distilled off after 6 hours. The remaining residue of 1,035 g of vinylphosphonic acid derivatives is cooled, and 5.7 g of potassium hypophosphite are added at 95° C., whilst stirring. The reaction material then slowly cools to room temperature.

298 g of the vinylphosphonic acid derivatives thus prepared are metered into 300 g of vinylphosphonic acid dichloride at 145° C. during the course of 4 hours, whilst stirring, during which time phosgene gas is continuously introduced into the reaction mixture. The reaction mixture is then further phosgenated for 10 hours at this temperature. 1,2-Dichloroethane which is formed distils off during the phosgenation. After the phosgenation has ended, the excess phosgene is stripped off at room temperature in the vacuum from a water jet.

The mixture is then distilled at 2 mm Hg with the aid of a column. 430 g of vinylphosphonic acid dichloride and 140 g of 2-chloroethanephosphonic acid dichloride are obtained. The distillation residue is 39 g. 130 g of vinylphosphonic acid dichloride and 140 g of 2-chloroethanephosphonic acid dichloride were thus prepared from 298 g of vinylphosphonic acid derivatives. The 2-chloroethanephosphonic acid dichloride can again be employed as the reaction medium in a second mixture, instead of the vinylphosphonic acid dichloride.

EXAMPLE 4

2 g of sodium carbonate are suspended in 950 g of the Arbusow mixture, as employed in Example 1. 500 g of such a mixture are heated to 192° C. under a nitrogen atmosphere, whilst stirring. 1,2-Dichloroethane begins to distil off. The remaining 450 g of the mixture are now added dropwise at this temperature, whilst 1,2-dichloroethane distils off. At the end of the reaction, the mixture is heated to 202° C. 400 g of 1,2-dichloroethane have distilled off after 4.5 hours. 549 g of vinylphosphonic acid derivatives remain.

300 g of the vinylphosphonic acid derivatives thus prepared are metered into 300 g of vinylphosphonic acid dichloride at 145° C. during the course of 4 hours, whilst stirring, during which time phosgene gas is continuously introduced into the reaction mixture. The mixture is then further phosgenated for 11 hours at this temperature. 1,2-Chloroethane which has formed distils off during the phosgenation. After the phosgenation has ended, the excess phosgene is stripped off at room temperature in the vacuum from a water jet. The mixture is then distilled at 2 mm Hg with the aid of a column. 410 g of vinylphosphonic acid dichloride and 155 g of 2-chloroethanephosphonic acid dichloride are obtained. The distillation residue is 46.5 g. 110 g of vinylphosphonic acid dichloride and 155 g of 2-chloroethanephosphonic acid dichloride were thus prepared from 300 g of vinylphosphonic acid derivatives. The 2-chloroethanephosphonic acid dichloride can again be employed as the reaction medium in a second mixture, instead of vinylphosphonic acid dichloride.

EXAMPLE 5

120 g of bis-2-chloroethyl 2-chloroethanephosphonate are heated to 208° to 215° C., whilst stirring. 59 g of 1,2-dichloroethane distils off during the course of 5 hours. 59 g of vinylphosphonic acid derivatives remain. (Acid number: 371, iodine number: 144; 22.7% of phosphorus, 7.4% of chlorine). These derivatives are reacted with phosgene, as in Example 1. 57 g of vinylphosphonic acid dichloride are obtained.

EXAMPLE 6

120 g of non-distillable polycondensates, as produced in the Arbusow rearrangement of tris-chloroethyl phosphite and having a proportion of 32% of 2-chloroethanephosphonic acid 2-chloroethyl ester 2-(bis-(2-chloroethoxy)-phosphono)-ethyl ester are heated to 200° C., whilst stirring. 41 g of 1,2-dichloroethane with a content of 0.8% of hydrogen chloride split off in the course of 6 hours. 76 g of vinylphosphonic acid derivatives are obtained. (Acid number: 338, iodine number: 148). These derivatives are reacted with phosgene as in Example 1. 65 g of vinylphosphonic acid dichloride are obtained.

EXAMPLE 7

135 g of bis-2-chloroethyl 2-chloroethanephosphonate and 4 g of phosphoric acid trisdimethylamide are heated to 185°–190° C. for 5 hours, whilst stirring. 66 g of 1,2-dichloroethane distil off during this process. A vacuum of 35 mm Hg is then applied for 6 hours. A further 6 g of 1,2-dichloroethane condense in a cold trap downstream from the apparatus. 65.5 g of vinylphosphonic acid derivatives remain. (Acid number: 374, iodine number: 121; 24.1% of phosphorus, 1.5% of chlorine). These compounds are reacted with phosgene, as described in Example 1. 63 g of vinylphosphonic acid chloride are obtained.

EXAMPLE 8

85.3 g of non-distillable polycondensates, as used in Example 6, and 1.7 g of 1,4-diazabicyclo[2,2,2]-octane ("Dabco") are heated to 185° to 190° C. during the course of 5 hours, whilst stirring. 32 g of 1,2-dichloroethane distil off during the course of 5 hours. 54 g of vinylphosphonic acid derivatives are obtained (acid number 368, iodine number: 124; 23.1% of phosphorus, 5.1% of chlorine). These compounds are reacted with phosgene, as described in Example 1. 49 g of vinylphosphonic acid dichloride are obtained.

EXAMPLE 9

85.3 g of non-distillable polycondensates, as used in Example 6, and 2 g of 1-methyl-1-oxo-$\Delta^3$-phospholene are heated to 180° -190° C. during the course of 13 hours, whilst stirring. 29.5 g of 1,2-dichloroethane distil off. 53 g of vinylphosphonic acid derivatives remain (acid number: 383, iodine number: 133; 24.5% of phosphorus, 4.7% of chlorine). These compounds are reacted with phosgene, as in Example 1. 49 g of vinylphosphonic acid dichloride are obtained.

We claim:

1. A process for the preparation of vinylphosphonic acid dichloride and 2-chloroethanephosphonic acid dichloride which consists essentially of heating a 2-chloroethanephosphonic compound containing 2-chloroethyl ester groups to 150°–230° C. in a first step, with cleavage of dichloroethane and formation of a vinylphosphonic compound as a reaction product of said first step, and in a second step, reacting the said reaction product with phosgene at 90°–200° C., in the presence of a basic catalyst, or of an alkali metal salt as catalyst, and in the presence of a phosphonic acid dichloride.

2. A process as claimed in claim 1, wherein the reaction is carried out in the first step in the presence of an acid or basic catalyst.

3. A process as claimed in claim 1, wherein the reaction is carried out in the first step at 170° to 215° C. and in the 2nd step at 120° to 170° C.

4. A process as claimed in claim 1, wherein the reaction is carried out in the second step in the presence of a mixture of vinylphosphonic acid dichloride and 2-chloroethanephosphonic acid dichloride.

5. A process according to claim 1 wherein said first step is carried out with formation of a mixture of vinylphosphonic acid compounds as reaction products of said first stage, and, in a second step, reacting this mixture with phosgene at 90°–200° C.

* * * * *